United States Patent [19]
Ganshorn

[11] Patent Number: 5,620,005
[45] Date of Patent: Apr. 15, 1997

[54] CALIBRATION APPARATUS FOR THE PRESSURE GAUGES OF A WHOLE-BODY PLETHYSMOGRAPH

[76] Inventor: Peter Ganshorn, Goldgrund 5, D-97702 Münnerstadt, Germany

[21] Appl. No.: 557,779

[22] Filed: Nov. 13, 1995

[30] Foreign Application Priority Data

Nov. 12, 1994 [DE] Germany ............... 44 40 482.4

[51] Int. Cl.⁶ .................................................. A61B 5/08
[52] U.S. Cl. ...................... 128/716; 128/718; 73/149; 73/1.66; 73/1.68
[58] Field of Search ........................... 128/716, 720, 128/725–728, 730; 73/149, 4 R, 4 V

[56] References Cited

U.S. PATENT DOCUMENTS

| | | | |
|---|---|---|---|
| 2,569,849 | 10/1951 | Emerson | 128/728 |
| 5,105,825 | 4/1992 | Dempster | 128/774 |
| 5,379,777 | 1/1995 | Lomask | 128/716 |

FOREIGN PATENT DOCUMENTS

| | | | |
|---|---|---|---|
| 2647028 | 4/1978 | Germany | 128/730 |

*Primary Examiner*—Angela D. Sykes
*Assistant Examiner*—Bryan K. Yarnell
*Attorney, Agent, or Firm*—Edwin D. Schindler

[57] ABSTRACT

A whole-body plethysmograph having a calibration of the pressure gauge is provided, which includes an air tight, lockable cubicle for the reception of a person to be examined, a cubicle-pressure pressure gauge that responds to the interior pressure of the cubicle. A mouthpiece is provided with a valve, by means of which the respiratory air flow can be barred, and a closure-pressure pressure gauge is connected to the mouthpiece for measuring the pressure in the mouth of a person, as well as an evaluation unit connected to both the cubicle-pressure pressure gauge and the closure-pressure pressure gauge. A piston pump is connected to said cubicle, so as to be air tight. The piston pump is surrounded by the air tight box, to which the closure-pressure pressure gauge is, at times, connected for calibration and the pressure fluctuations generated by the piston pump are used to calibrate the cubicle-pressure pressure gauge and the closure-pressure pressure gauge.

7 Claims, 1 Drawing Sheet

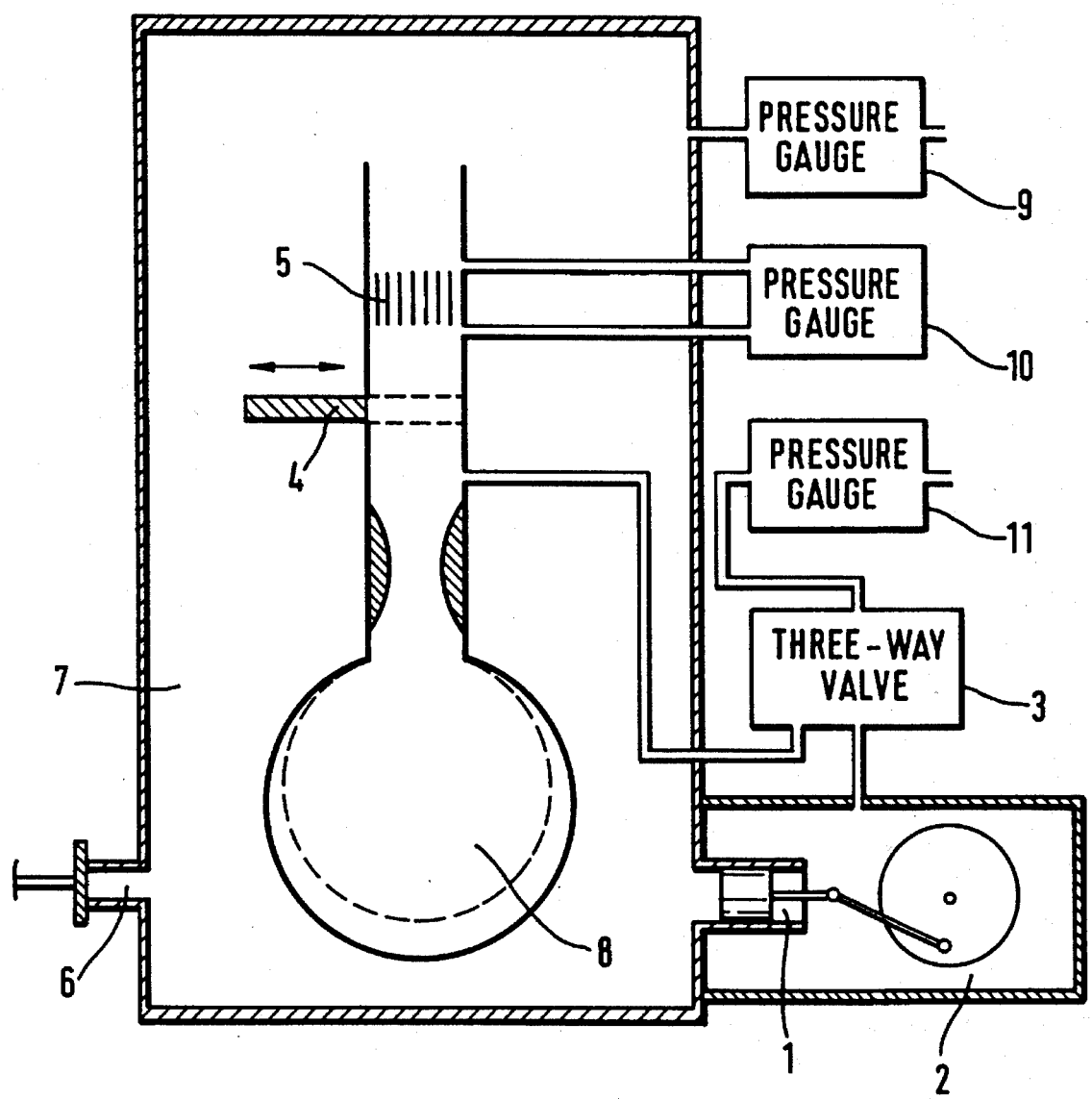

CALIBRATION APPARATUS FOR THE PRESSURE GAUGES OF A WHOLE-BODY PLETHYSMOGRAPH

BACKGROUND OF THE INVENTION

1. Technical Field of the Invention

The present invention relates to a whole-body plethysmograph having calibration of the pressure gauge, comprising an air tight, lockable cubicle for the reception of a person to be examined, a cubicle-pressure pressure gauge that responds to the interior pressure of the cubicle, a mouthpiece with a valve, by means of which the respiratory flow can be barred and a closure-pressure pressure gauge connected to the mouthpiece to measure the pressure in the mouth of the person, as well as an evaluation unit connected to both pressure gauges.

2. Description of the Prior Art

A plethysmograph is known in the art as an apparatus for measuring the changes in the volume of an organ or a part of the body. The whole-body plethysmograph serves especially well to measure changes in the volume of the thorax-lung system. Various examination methods are possible and are often combined. One known method consists of measuring the interior pressure of the cubicle and the respiratory flow rate, whereby conclusions can be drawn about the alveolar pressure and the bronchial airway resistance. Another method consists of measuring, with barred respiratory flow, both the pressure in the thorax-lung system, as well as in the cubicle. The patient breathes voluntarily against the closure and, thus, changes his lung volume. With knowledge of the gas laws, important results can be determined from the measured fluctuations in pressure. Thus, the residual volume of the lung (thoracal gas volume) can be defined.

A major drawback with plethysmography concerns accurately calibrating the pressure absorber, both at the mouth of the test person as well as in the chamber. An exact calibration and adjustment is required because the relative pressure differences are very small and, therefore, possible disturbing influences must be eliminated. It is, therefore, possible that the pressure gauge has a specific frequency dependency. The methods used by the prior art for calibration are inexact, laborious and complicated and could frequently not be executed by the medical operating personnel in a satisfactory manner. Here calibration of the closure-pressure pressure gauge was effected in a static manner by means of a constantly specified pressure and, thus, fully independently of the cubicle-pressure calibration.

SUMMARY OF THE INVENTION

It is, therefore, an object of the present invention to provide a whole-body plethysmograph, wherein the pressure gauge can be readily calibrated by auxiliary medical personnel.

The foregoing and related objects are achieved by the whole-body plethysmograph of the present invention, which provides a piston pump connected in an air tight manner to the cubicle, which itself is surrounded by an air tight box, to which the closure-pressure pressure gauge is, at times, connected for calibration, with the pressure fluctuations created by the piston pump being used for calibrating the pressure gauge.

A central concept of the present invention concerns reproducing the thorax-lung system by means of the box. The fluctuations in pressure required for calibration are generated by the piston pump. The movement of the piston from the box to the cubicle corresponds to inspiration: The volume of the box is enlarged and the volume of the cubicle is reduced. Vice versa, the movement of the piston from the cubicle to the box corresponds to expiration. The box has a known gas volume; likewise, the piston pump has a known piston capacity and runs at a known frequency. From these quantities, the desired pressure fluctuations can be calculated and, thus the pressure gauges calibrated; one of which measures the pressure in the box and the other, the pressure in the cubicle.

The apparatus can, thus, be adjusted so that when switched on the calibration process runs automatically every time. Upon termination of calibration, the closure-pressure pressure gauge is separated from the box and connected to the mouthpiece. Separation and connection can be done, for example, by simply detaching and fixing a hose or, more comfortably, by switching a three-way valve.

The advantages of the present invention lie, above all, in that calibration is easier to execute and that operational errors connected with calibration are ruled out. A further decisive advantage arises whereby on both sides of the piston pump, the same volume is always impinged in counter-rotation, thereby corresponding exactly to the breathing process under measurement conditions. This type of calibration is, thus, to be considered as optimum.

In a preferred embodiment of the present invention, the frequency of the pump is adjustable. Since the usual breathing rate lies between 0.5 and 2 Hz, the pump is at least controllable within this range. It is now possible to create a calibration curve in dependency on the frequency. In this manner, losses or nonlinearities of the pressure gauge occurring at a specific frequency can be recorded and considered.

The average theoracal gas volume is more or less 3 to 4 liters. In order to approximate the measurement conditions as best as possible during calibration, it is therefore proposed to dimension the box so that it contains a volume of gas of 3 to 4 liters.

For the same reason, the piston capacity of the pump is advantageously adjusted to the fluctuations in body volume during breathing.

Finally, it is also appropriate to design the whole-body plethysmograph so that the volume of the cubicle and, above all, that of the box, is modifiable, which adapts the box volume to the lung volume of the patient and, therefore, allows calibration to be further optimized. The changes in volume are achieved by the connection or sealing off of additional volumes.

Other objects and features of the present invention will become apparent when considered in combination with the accompanying drawing figures which illustrate certain preferred embodiments of the present invention. It should, however, be noted that the accompanying drawing figures are intended to illustrate only certain embodiments of the claimed invention and are not intended as a means for defining the limits and scope of the invention.

BRIEF DESCRIPTION OF THE DRAWING FIGURES

The single drawing FIG. 1, is a schematic diagram of a preferred embodiment of the whole-body plethysmograph of the present invention.

DETAILED DESCRIPTION OF THE DRAWING FIGURE AND PREFERRED EMBODIMENTS

The accompanying drawing figure shows a whole-body plethysmograph according to the present invention, which comprises an air tight, lockable cubicle 7. An air tight box 2 is affixed to cubicle 7; box 2 having a cylindrical opening to cubicle 7 in which a piston is disposed, which is moved along the cylinder axis by a drive disposed in box 2. The drive, which includes a rotating disc and transmission rods, forms, with the piston, a harmoniously oscillating piston pump 1. Box 2 serves to reproduce the thorax-lung system and, consequently, has approximately the same gas volume as the lung. During the calibration process, it is connected to a closure-pressure pressure gauge 11 via a three-way valve 3.

During the measuring process, three-way valve 3 is switched so that the closure-pressure pressure gauge 11 is connected to the mouthpiece and measures the pressure in the thorax-lung system. During the closure-pressure measurement, a valve 4 (shown in an open position is the drawing figure) in the mouthpiece is closed. The thorax-lung system is represented in the drawing figure by a diagrammatic lung model 8.

Furthermore, the mouthpiece has a pneumo-tachometer 5, which is disposed in the direction of expiration behind valve 4 and is connected to a streaming-pressure pressure gauge 10, which, although not required for the closure-pressure measurement, is necessary for the measurement of the flow resistance, which is mostly executed in combination with the closure-pressure measurement. Cubicle 7 also has a shutter valve 6 and a connection to a cubicle-pressure pressure gauge 9. All pressure gauges (9, 10, 11) are connected to an evaluation unit.

While only several embodiments of the present invention have been shown and described, it will be obvious to those skilled in the art that many modifications may be made to the present invention without departing from the spirit and scope thereof.

What is claimed is:

1. A whole-body plethysmograph having calibration of a pressure gauge, comprising:

an air tight, lockable cubicle for reception of a person to be examined;

a cubicle-pressure pressure gauge which responds to an interior pressure of said lockable cubicle;

a mouthpiece having a valve, by which respiratory air flow is capable of being barred;

a closure-pressure pressure gauge connected to said mouthpiece for measuring pressure in a mouth of the person being examined;

an evaluation unit connected to said cubicle-pressure pressure gauge and said closure-pressure pressure gauge for evaluating a volume of a person's lungs based upon a measured pressure value;

an air tight box being affixed, via a cylindrical opening, to said lockable cubicle; and, a piston pump connected in an air-tight manner to said lockable cubicle, said piston pump being surrounded by said air tight box, to which said closure-pressure pressure gauge is, during certain time intervals, connected for calibration with pressure fluctuations generated by said piston pump being used to calibrate said cubicle-pressure pressure gauge and said closure-pressure pressure gauge.

2. The whole-body plethysmograph having calibration of a pressure gauge according to claim 1, wherein said closure-pressure pressure gauge is connected to said air tight box for a calibration in measuring the pressure in the mouth of the person being examined, whereupon termination of calibration, said closure-pressure pressure gauge is separated from the air tight box and connected to said mouthpiece.

3. The whole-body plethysmograph having calibration of a pressure gauge according to claim 1, wherein said piston pump has a frequency that is adjustable in the range of 0.5 to 2 Hz.

4. The whole-body plethysmograph having calibration of a pressure gauge according to claim 1, wherein said air tight box has a gas volume of 3–4 liters.

5. The whole-body plethysmograph having calibration of a pressure gauge according to claim 1, wherein said piston pump has a piston capacity substantially corresponding to the average fluctuations in body volume during breathing.

6. The whole-body plethysmograph having calibration of a pressure gauge according to claim 1, wherein said lockable cubicle has a volume which is able to be modified by connectable additional volumes.

7. The whole-body plethysmograph having calibration of a pressure gauge according to claim 1, wherein said air tight box has a volume which is able to be modified by connectable additional volumes.

\* \* \* \* \*